(12) United States Patent
Kross et al.

(10) Patent No.: US 8,217,359 B1
(45) Date of Patent: Jul. 10, 2012

(54) COLLIMATOR WITH ATTACHMENT MECHANISM AND SYSTEM

(75) Inventors: Brian J. Kross, Yorktown, VA (US); John McKisson, Hampton, VA (US); Aleksandr Stolin, Morgantown, WV (US); Andrew G. Weisenberger, Yorktown, VA (US); Carl Zorn, Yorktown, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 0 days.

(21) Appl. No.: 13/135,615

(22) Filed: Jul. 11, 2011

(51) Int. Cl.
*G21K 1/02* (2006.01)
*H01J 5/18* (2006.01)

(52) U.S. Cl. .............. 250/370.09; 250/482.1; 250/505.1; 250/503.1; 378/147; 378/149; 378/151

(58) Field of Classification Search ............. 250/370.08, 250/370.09, 396 R, 482.1, 503.1, 505.1, 526; 378/145, 147, 149, 151
See application file for complete search history.

(56) References Cited

U.S. PATENT DOCUMENTS

| | | | | |
|---|---|---|---|---|
| 5,847,398 | A * | 12/1998 | Shahar et al. | 250/370.09 |
| 7,141,812 | B2 * | 11/2006 | Appleby et al. | 250/505.1 |
| 7,411,204 | B2 * | 8/2008 | Appleby et al. | 250/505.1 |
| 7,462,852 | B2 * | 12/2008 | Appleby et al. | 250/505.1 |
| 7,462,854 | B2 * | 12/2008 | Pinchot | 250/506.1 |
| 7,518,136 | B2 * | 4/2009 | Appleby et al. | 250/505.1 |
| 7,838,856 | B2 * | 11/2010 | Pinchot | 250/515.1 |
| 7,893,413 | B1 * | 2/2011 | Appleby et al. | 250/505.1 |
| 8,049,193 | B1 * | 11/2011 | Appleby et al. | 250/505.1 |

* cited by examiner

*Primary Examiner* — Bernard E Souw

(57) ABSTRACT

A self-aligning collimator for a radiation imaging device that is secured and aligned through the use of a plurality of small magnets. The collimator allows for the rapid exchange, removal, or addition of collimators for the radiation imaging device without the need for tools. The accompanying method discloses the use of magnets and accompanying magnetic fields to align and secure collimators in a radiation imaging assembly.

15 Claims, 2 Drawing Sheets

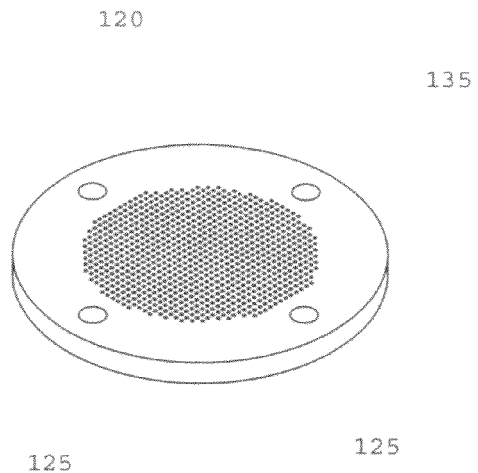
FIG. 3b
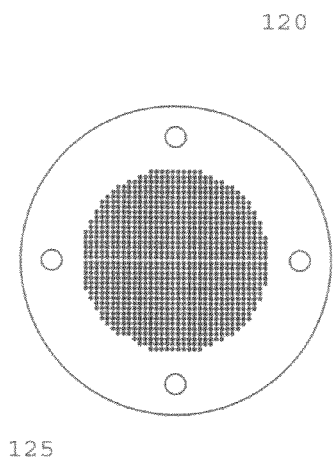
FIG. 4
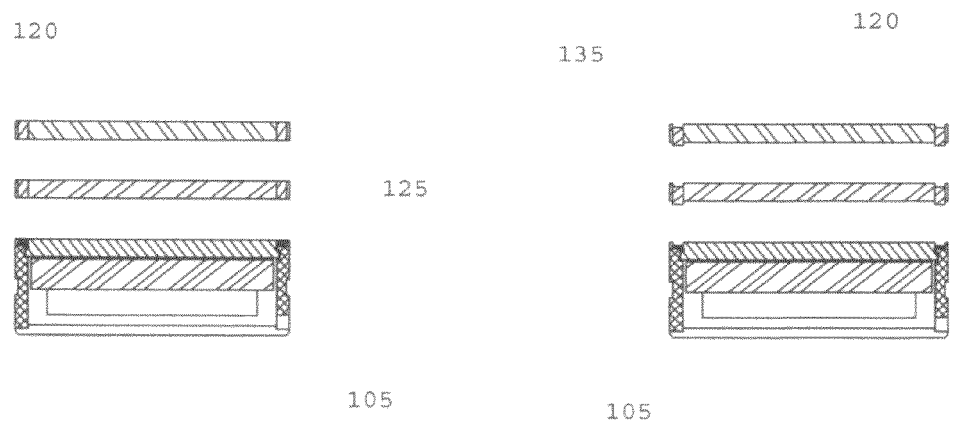
FIG. 5
FIG. 6

COLLIMATOR WITH ATTACHMENT MECHANISM AND SYSTEM

The United States of America may have certain rights to this invention under Management and Operating Contract No. DE-AC05-84ER 40150 from the Department of Energy.

FIELD OF THE INVENTION

The present invention relates to a device and method for attaching one or more collimators in a radiation imaging system.

BACKGROUND OF THE INVENTION

Medical imaging through the use of radionuclides has become a critical component in the diagnosis and treatment of many diseases and conditions. A device, such as a gamma camera, can be used to detect radiation emitted from radioisotopes. These types of devices are often used by physicians within a sterile surgical field.

One or more collimators are typically employed in such a device in order to facilitate the desired imaging. A collimator can be used to reduce stray or unwanted radiation so that it does not reach the detector portion of the imaging device. Stray or scattered radiation, e.g., radiation that is not travelling parallel from the imaged area, may significantly impair the resolution of the device.

In certain types of radiation imaging, it is necessary to frequently change collimators. Collimators may be changed for several reasons, including adapting the radiation imager to a different energy, changing its resolution or count rate, or changing the angle of view.

A surgeon may have the desire to initially operate the gamma camera at a rapid speed, with low resolution, as he begins the process of localizing a target area. In such cases, the gamma camera might be operated with simply one collimator attached. Once the surgeon approaches a suspect lesion, he may wish to increase the resolution of the device. He may then add one or more additional collimators until the desired resolution is achieved.

In traditional assemblies, the collimators are retained by screws within flanges. With intraoperative radiation imagers, the devices are usually operated within a disposable sheath or sleeve in order to maintain the integrity of the sterile field. The use of a sleeve is a preferred method of operation as sterilization of the entire gamma camera assembly is more problematic due to the numerous surfaces and crevices on the assembly. If a different collimator is required, the device must be removed from the sterile field, the collimator changed using tools, the device inserted in a new sterile sheath, and then returned to the sterile field. This method of exchange is time-intensive and may result in a disruption of the surgical procedure. The use of screws/flanges has further drawbacks in that it requires an inert area within the collimator structure that in some cases inhibits the optimum use of the collimator.

It is therefore preferable to have a collimator that can be easily and quickly changed. It is further desirable to have a device and method which insures the accurate and precise positioning of the collimators in the assembled radiation imager.

OBJECT OF THE INVENTION

It is an object of the invention to provide a collimator design and a method of attachment which permits a user to rapidly and effectively exchange, add, or remove collimators from a radiation imaging device, particularly one that is being used inter-operatively.

SUMMARY OF THE INVENTION

The present invention discloses a self-aligning collimator that is secured to other collimators on a radiation imaging device through the use of a plurality of small magnets. The magnets allow a user to rapidly exchange collimators. The disclosed collimator uses the magnetic field of the magnets in order to guide the collimators into an appropriate axial alignment and to insure proper rotational orientation.

BRIEF DESCRIPTION OF THE DRAWINGS

FIG. 4 is a plane top view of an additional collimator.

FIG. 5 is a side view of a preferred embodiment of a gamma camera assembly with attached collimators.

FIG. 6 is a side view of an alternate embodiment of a gamma camera assembly with attached collimators.

DETAILED DESCRIPTION

The present invention discloses a device and method for securing and aligning collimators to a radiation imaging assembly such as a gamma camera. In many common applications, multiple collimators are used in the imaging device. These collimators are stacked on top of one another in a particular alignment and orientation. When stacking collimators in such a fashion, it is essential to maintain their position relative to both one another and the radiation imaging assembly. The present invention facilitates the replacement, addition, or removal of such additional collimators on the imaging assembly.

Figure 1:
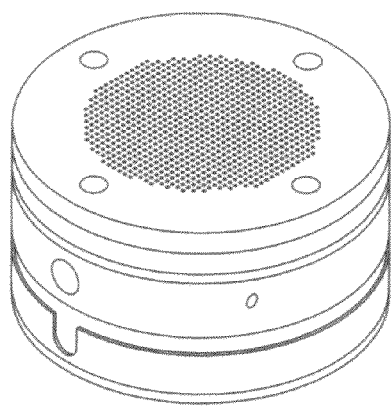
FIG. 1 is a perspective view of a gamma camera assembly.
Figure 2A:
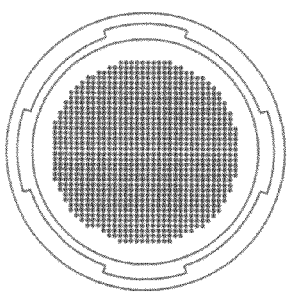
FIG. 2 shows the bottom (2a) and top (2b) of a base collimator.
Figure 2B:
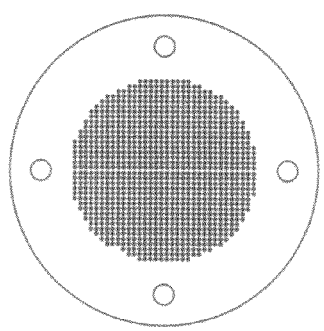

In operation, a radiation imaging device such as the gamma camera 100 depicted in FIG. 1, may utilize one or more collimators 105 and 110. A base collimator 105 is secured to the gamma camera 100 through the use of a bayonet-type mount or similar structure as seen in FIG. 2a. In a preferred embodiment, the base collimator 105 includes a first portion of a bayonet mount 115. The gamma camera base includes a second portion of the bayonet mount, i.e., slots, designed to receive and secure the first portion of the mount. The bayonet mount may be made of brass or any other suitable material.

Figure 3A:
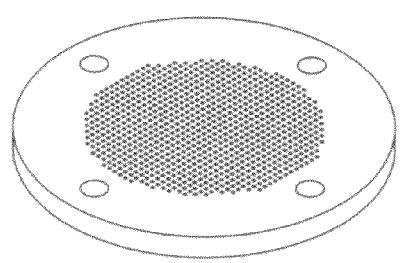
FIG. 3 shows a perspective view of an additional collimator: front (3a) and back (3b).

Additional or extra collimators may then be easily added to the gamma camera assembly and base collimator through the use of magnets. Referring now to FIG. 3a, each additional collimator disk 120 incorporates four magnets 125 of appropriate strength. When an additional collimator disk is to be attached, each such magnet is subsequently attached to a corresponding magnet on the additional collimator disk. Accordingly, four pairs of magnets are used to secure and align the collimator disks.

Each magnet 125 is embedded at a pre-determined location in the collimator disk 120. Therefore, each magnet 125 is essentially flush with the top 130 and bottom 135 surfaces of the collimator, as shown in FIGS. 3a and 3b. Further, each magnet 125 would be located such that each would be in alignment with magnets of additional collimator disks that may be positioned above or below a particular disk. FIG. 4 shows a plan view of an additional collimator disk 120.

Each collimator disk beyond the base disk 105 must be precisely aligned with the gamma camera 100 and other collimator disks. In traditional collimator arrangements, e.g., where mounting screws are used, the collimator disks must be physically moved into proper alignment so as to permit the installation of the screws.

In the preferred embodiment of the invention shown in FIG. 5, the magnetic field of the magnets 125, rather than hand placement, is used for alignment. The magnetic field of the magnets 125 serves to axially align the collimators within acceptable limits. As an example, if the collimator placement on the assembly is off by ¼ mm, the magnetic field will pull the collimator into proper axial alignment at a 0, 0 (x, y) coordinate position relative to the collimators and radiation imaging assembly. The magnets 125 are mounted in holes in the collimator body.

In an alternate embodiment, shown in FIG. 6, the magnets 135 are not flush with the collimator surfaces. In this alternate embodiment, each magnet 135 is positioned within the hole such that the bottom portion of the magnet projects outward from the bottom side of the collimator surface for a short distance. This positioning also results in the creation of a small aperture or depression 140 on the top surface of the collimator. The aperture or depression 140 on the top surface of the collimator then serves to receive the magnet 135 extension from an additional collimator if further stacking is desired.

In such an embodiment, the magnets 135, in essence, also act as dowels. Each collimator disk 145, 150, 155 is then axially aligned and further secured by placing the protruding portion of the magnets 135 in the appropriate corresponding aperture on another respective collimator disk.

Rotational orientation of the collimators is also critical in the imaging assembly. Proper rotational orientation can be achieved in more than one fashion. In the preferred embodiment, the rotational alignment is achieved through a particular arrangement of the polarity of the magnets. As mentioned earlier, four pair of magnets may be used. In such case, the respective poles of the pairs of magnets are oriented as north/south and south/north. As a result of the foregoing arrangement, if two collimators are placed together such that they are rotated 180 degrees out of alignment, the two collimators will not remain secured together and will simply fall apart. In order to rectify that problem, the user will have to spin one of the collimators around to the correct alignment, i.e., until the correct pairs are aligned up, and they will lock on.

In an alternate embodiment, one pair of the magnets is installed a few degrees out of alignment. In this alternate embodiment, if a user attempts to place a collimator disk in an incorrect rotational alignment, the magnets will force the disk noticeably out of axially alignment and a user would be alerted as to the improper rotational positioning.

When used inter-operatively, the addition, removal, or substitution of collimators may be accomplished while the gamma camera remains in the sterile surgical field and the device is still retained within the sleeve. A user can actually leave or stack additional collimator disks in the sleeve—at a location further up the sleeve. The additional collimator disks can then be slipped into place as necessary. Once the additional collimator disk is placed somewhat near the proper positioning, it will simply click into place. The magnetic field will insure proper alignment and will further secure the additional collimator without the need for removal of the device from the sheath or the use of tools.

In addition, the elimination of the mounting screws and flanges serves to provide smoother surfaces on the gamma camera device. Smoother surfaces are preferable in order to reduce the likelihood of retaining bacteria or other such contamination on the exterior of the device.

While the invention has been described in reference to certain preferred embodiments, it will be readily apparent to one of ordinary skill in the art that certain modifications or variations may be made to the system without departing from the scope of invention claimed below and described in the foregoing specification.

What is claimed is:

1. A self-aligning collimator for a radiation imaging device comprising:
   a body with a top surface and a bottom surface; and
   a plurality of magnets incorporated into said body,
   wherein said magnets are positioned such that said magnets may serve to secure and align said collimator with another collimator of substantially similar design.

2. The self-aligning collimator of claim 1 wherein said plurality of magnets comprises at least three magnets.

3. The self-aligning collimator of claim 1 wherein said plurality of magnets comprises no less than four magnets.

4. The self-aligning collimator of claim 1 wherein said collimator is of a substantially circular design.

5. The self-aligning collimator of claim 4 wherein said plurality of magnets are positioned essentially adjacent to the circumference of said collimator.

6. The self-aligning collimator of claim 4 wherein said plurality of magnets comprises a first pair of magnets and a second pair of magnets.

7. The self-aligning collimator of claim 6 wherein said first pair of magnets includes a first magnet and a second magnet; said first magnet being located at a position near the periphery of said collimator; said second magnet being located near the periphery of said collimator at a point antipodal to said first magnet.

8. The self-aligning collimator of claim 7 wherein said second pair of magnets includes a third magnet and a fourth magnet; said third magnet being located at a position near the periphery of said collimator; said fourth magnet being located near the periphery of said collimator at a point antipodal to said third magnet.

9. The self-aligning collimator of claim 4 wherein said magnets may be used to secure and align another collimator of substantially similar design on either the top surface or the bottom surface of said self-aligning collimator.

10. The self-aligning collimator of claim 4 wherein said magnets may be used to secure and align a collimator of substantially similar design to said top surface and a second collimator of substantially similar design to said bottom surface.

11. The self-aligning collimator of claim 4 wherein said magnets are essentially flush with said top surface and said bottom surface of said collimator.

12. The self-aligning collimator of claim 4 wherein said magnets are positioned such that said magnets extend beyond the plane of the bottom surface of said collimator and the positioning of said magnets results in the creation of a plurality of depressions on the top surface of said collimator; said plurality of depressions being disposed to receive magnets from another collimator of substantially similar design.

13. A method of aligning and securing two or more collimators in a radiation imaging device comprising:
   providing a first collimator having a first pair of magnets and a second pair of magnets incorporated therein;
   providing a second collimator of identical structure to said first collimator and having a first pair of magnets and second pair of magnets incorporated therein;

placing said first collimator and said second collimator in proximity; and securing and axially and rotationally aligning said first and second collimators through the use of the magnetic fields exerted by said first and second pairs of magnets on said first collimator and said first and second pairs of magnets on said second collimator.

14. A method of aligning and securing two or more collimators in a radiation imaging device comprising:

providing a first collimator with a top surface and a bottom surface; said bottom surface including a mount to secure said first collimator to said radiation imaging device; said first collimator having a first pair of magnets and a second pair of magnets;

providing a second collimator having a first pair of magnets and a second pair of magnets incorporated therein;

securing said first collimator to said radiation imaging device with said mount;

placing said second collimator in proximity to said first collimator; and securing and axially and rotationally aligning said first and second collimators through the use of the magnetic fields exerted by said first and second pairs of magnets on said first collimator and said first and second pairs of magnets on said second collimator.

15. The method of claim 14 further comprising:

identifying the last collimator attached to said radiation imaging device as the top collimator;

providing one or more additional collimators identical in structure to said second collimator and having a first pair of magnets and second pair of magnets incorporated therein;

placing said one or more additional collimators in proximity to the top collimator attached to said radiation imaging device; and securing and axially and rotationally aligning said one or more additional collimators and said top collimator through the use of the magnetic fields exerted by said first and second pairs of magnets on said one or more additional collimators and said first and second pairs of magnets on said top collimator.

* * * * *